United States Patent
Cabiri

(10) Patent No.: US 9,138,566 B2
(45) Date of Patent: Sep. 22, 2015

(54) STEERING TOOL

(75) Inventor: Oz Cabiri, Macabim (IL)

(73) Assignee: Bendit Technologies Ltd., Petah Tikva (IL)

( * ) Notice: Subject to any disclaimer, the term of this patent is extended or adjusted under 35 U.S.C. 154(b) by 250 days.

(21) Appl. No.: 13/557,471

(22) Filed: Jul. 25, 2012

(65) Prior Publication Data

US 2013/0304035 A1 Nov. 14, 2013

Related U.S. Application Data

(63) Continuation-in-part of application No. 13/470,319, filed on May 13, 2012, now Pat. No. 8,684,953.

(51) Int. Cl.
*A61M 25/09* (2006.01)

(52) U.S. Cl.
CPC ..... *A61M 25/09* (2013.01); *A61M 2025/09083* (2013.01); *A61M 2025/09133* (2013.01)

(58) Field of Classification Search
CPC .............. A61M 25/09; A61M 2025/09083; A61M 2025/09133; A61M 2025/09175

USPC ............ 600/585; 604/164.13, 165.01, 165.02
See application file for complete search history.

(56) References Cited

U.S. PATENT DOCUMENTS

| 3,521,445 | A | * | 7/1970 | Grable | 60/639 |
| 3,802,440 | A | * | 4/1974 | Salem et al. | 128/200.26 |
| 7,313,445 | B2 | * | 12/2007 | McVenes et al. | 607/127 |
| 7,914,466 | B2 | * | 3/2011 | Davis et al. | 600/585 |
| 8,951,210 | B2 | * | 2/2015 | Miyata et al. | 600/585 |

* cited by examiner

*Primary Examiner* — Max Hindenburg
(74) *Attorney, Agent, or Firm* — Dekel Patent Ltd.; David Klein

(57) ABSTRACT

A steering tool including an internal tube disposed inside an external tube, the internal and external tubes being arranged for longitudinal axial movement relative to one another, wherein a distal end of the internal tube is fixedly joined to a distal end of the external tube, and at least one of the internal and external tubes is slotted near the distal end thereof, and wherein the longitudinal axial movement causes bending of the distal ends of the tubes.

6 Claims, 4 Drawing Sheets

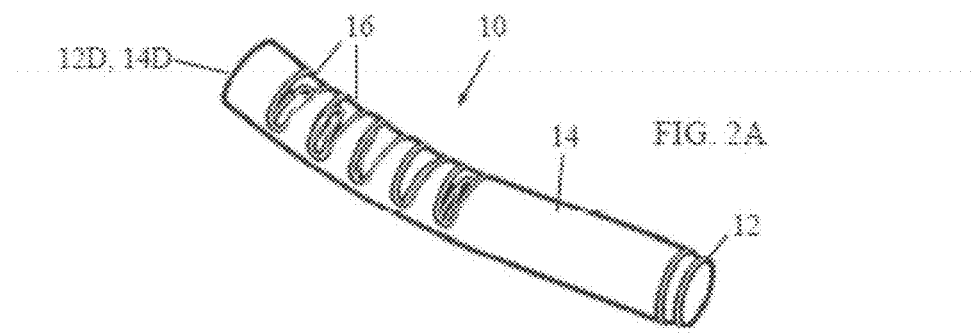
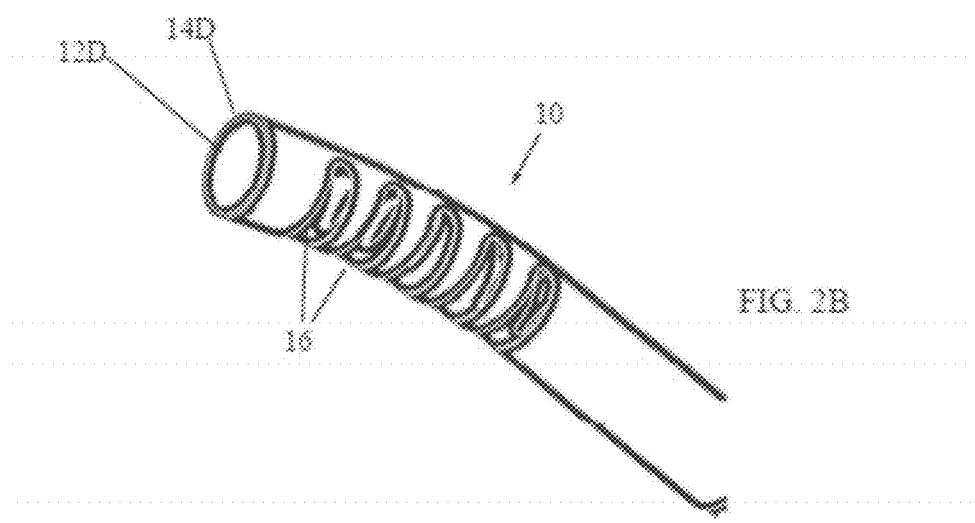
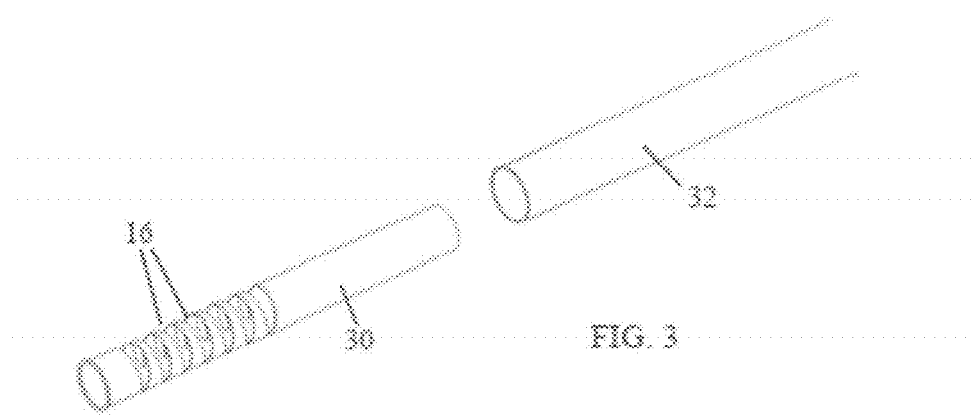

STEERING TOOL

CROSS REFERENCE TO OTHER APPLICATIONS

This application is a continuation-in-part of U.S. patent application Ser. No. 13/470,319, filed May 13, 2012.

FIELD OF THE INVENTION

The present invention generally relates to a steering tool for steering medical devices through body lumens.

BACKGROUND OF THE INVENTION

As is well known in the art, many medical procedures require steering a medical device through vasculature or other body lumens of a patient. One of the most common methods used involves passing a guidewire through the body lumen to a desired location. The medical device, such as a catheter, valve, stent, etc., is positioned by sliding over the guidewire to the desired location.

The lumen traversed by the guidewire can have various bends and branches. Sometimes, in order for the medical device to negotiate the bends and branches, not only must the guidewire be flexible, but also the medical device must have flexibility. However, delivery system curvature is not always desirable. Another problem is the device distal tip, which often must be bendable and steerable more than the rest of the device, yet the device must be constructed to allow application of torque to the tip.

SUMMARY OF THE INVENTION

The present invention seeks to provide an improved steering tool for steering medical devices through body lumens, as is described more in detail hereinbelow. The steering tool solves the abovementioned problems by providing a distal tip which combines steerability, flexibility and torqueability. The tool eliminates the need for pull/push wires.

One of the advantages of the present invention is its structure reduces the cross section of prior art steering tools that use push/pull wires. Another advantage is the ability to bend in different directions (at least two sides can bend and the device can be made for bending in more than two sides). The wall thickness can be very thin, such as 0.05 mm, but the invention is not limited to any thickness. The invention is effective for small tubes, such as but not limited to, diameters of 0.5-3 mm, and eliminates the need for ~0.2 mm manipulating wires and any space needed for extrusion. The invention is also effective with soft, thick tubes without any need for cutting.

There is thus provided in accordance with an embodiment of the present invention a steering tool including an internal tube disposed inside an external tube, the internal and external tubes being arranged for longitudinal axial movement relative to one another, wherein a distal end of the internal tube is fixedly joined to a distal end of the external tube, and at least one of the internal and external tubes is slotted near the distal end thereof, and wherein the longitudinal axial movement causes bending of the distal ends of the tubes.

In accordance with an embodiment of the present invention both of the internal and external tubes are slotted near the distal ends thereof.

In accordance with another embodiment of the present invention only one of the internal and external tubes is slotted, and the other tube is flexible, but not slotted.

In accordance with an embodiment of the present invention, for each of the tubes, the slots are generally perpendicular to a longitudinal axis of the tube.

In accordance with an embodiment of the present invention open ends of the slots of the external tube are oriented towards throats of the internal tube, and open ends of the internal tube are oriented towards throats of the external tube.

In accordance with another embodiment of the present invention, instead of a slotted tube, one of the tubes is flexible with relatively rigid stiffeners at a distal portion thereof.

BRIEF DESCRIPTION OF THE DRAWINGS

The present invention will be understood and appreciated more fully from the following detailed description taken in conjunction with the drawings in which:

FIGS. 2A and 2B are simplified illustrations of bending the steering tool of FIG. 1C;

FIG. 3 is a simplified illustration of a steering tool, in accordance with another non-limiting embodiment of the present invention, wherein only one of the internal and external tubes is slotted, and the other is flexible, but not slotted;

DETAILED DESCRIPTION OF EMBODIMENTS

Reference is now made to FIGS. 1 and 2, which illustrate a steering tool 10, in accordance with a non-limiting embodiment of the present invention.

Steering tool 10 includes an internal tube 12 disposed inside an external tube 14. A distal end 12D of internal tube 12 is fixedly joined to a distal end 14D of external tube 14. The term "joined" encompasses any method for attaching the materials of the tubes together, such as but not limited to, welding, ultrasonic welding, thermal bonding, adhesive bonding, molding, and others. Internal and external tubes 12 and 14 are arranged for longitudinal axial movement relative to one another.

Internal and external tubes 12 and 14 may be made of any suitably flexible, medically safe material, such as but not limited to, stainless steel (e.g., AISI 316), nitinol, cobalt-chromium alloy, nickel-titanium alloy, and others, plastics (e.g., nylon, polypropylene, and many others) or combinations thereof.

Figure 1A:
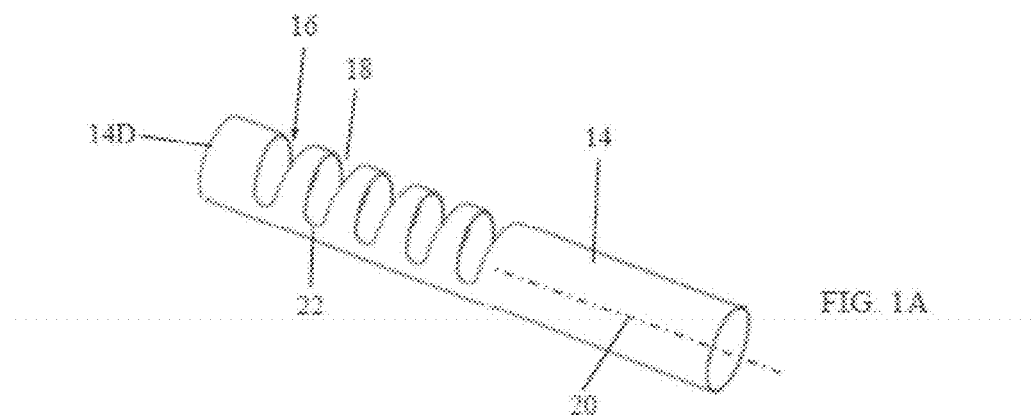
FIG. 1A is a simplified illustration of an external tube used in a steering tool, in accordance with a non-limiting embodiment of the present invention.
Figure 1B:
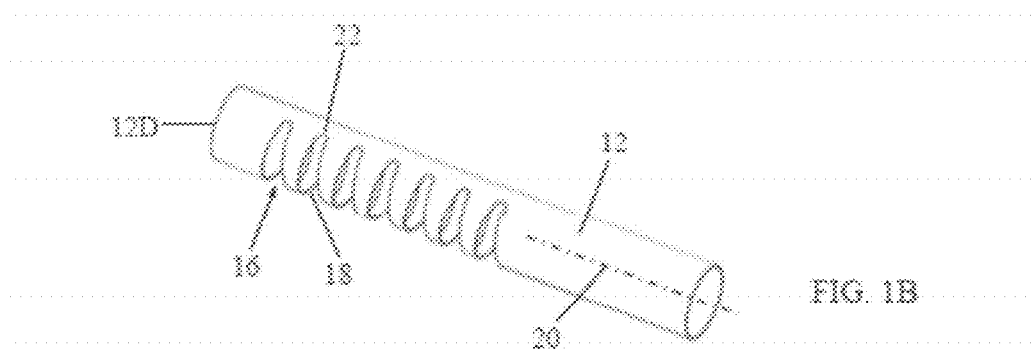
FIG. 1B is a simplified illustration of an internal tube used in the steering tool, in accordance with a non-limiting embodiment of the present invention, wherein both internal and external tubes are slotted.
Figure 1C:
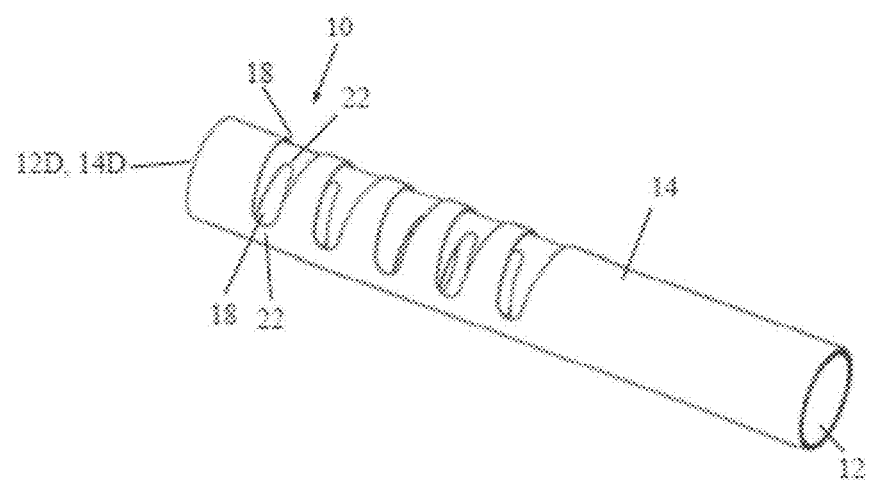
FIG. 1C is a simplified illustration of the assembled steering tool, in accordance with a non-limiting embodiment of the present invention.

At least one of the internal and external tubes 12 and 14 is slotted with slots 16 near the distal end thereof. In the embodiment of FIGS. 1A-1C, both tubes are slotted. In the embodiment of FIG. 3, only one of the internal and external tubes is slotted (reference numeral 30), and the other (reference numeral 32) is flexible, but not slotted. The longitudinal axial movement causes bending of the distal ends of the tubes, as seen in FIGS. 2A and 2B. As seen in FIG. 2A, one of the internal and external tubes can be longer than the other (in this case, the internal one is longer for grasping its proximal end for pushing and pulling thereof).

Slots 16 increase the flexibility toward the distal end of the tube or tubes for steerability of the device and controlled manipulation thereof. The amount of flexibility can be controlled by the number of slots, spacing therebetween, shape of the slot, angle subtended by the slot, thickness of the tube, material of the tube, and other factors.

Each slot 16 has an open end 18. In the illustrated embodiment, slots 16 are generally perpendicular to the longitudinal axis 20 of the tube. In other embodiments, the slots are non-perpendicular to the longitudinal axis 20 of the tube. The throat 22 of each slot 16 is shown as being wider than the open end 18. In other embodiments, throat 22 is not wider than the open end 18.

In the illustrated embodiment, slots 16 subtend an arc of about 180-270°, but the invention is not limited to this range. The remaining portion of the tube is left intact, so there is sufficient mechanical strength to prevent buckling or other mechanical failure.

In the illustrated embodiment, in the finished assembly of FIG. 1C, the open ends 18 of the external tube 14 are oriented towards the throats 22 of the internal tube 12; conversely, the open ends 18 of the internal tube 12 are oriented towards the throats 22 of the external tube 14. It is noted that the slots can be oriented at different orientations other than that illustrated in FIG. 1C (e.g., the throats and open ends are aligned at different angles and spacings, the slots are shaped differently, etc.) to arrive at bending modes in more than one direction in three-dimensional space. If both internal and external tubes are slotted, the slots can be in the same orientation. Alternatively and more preferably, the slots of the internal tube are not aligned with the slots of the external tube (there can be situations where aligned slots interfere and inhibit movement of the tube).

In the illustrated embodiment, the slots are equally spaced, sized and shaped, but other variations in spacing, size and shape can be used to achieve different properties.

Some non-limiting examples of different sizes and arrangements of slotted portions and non-slotted portions are now described with reference to FIGS. 5A-5B and 6.

Figure 5A:
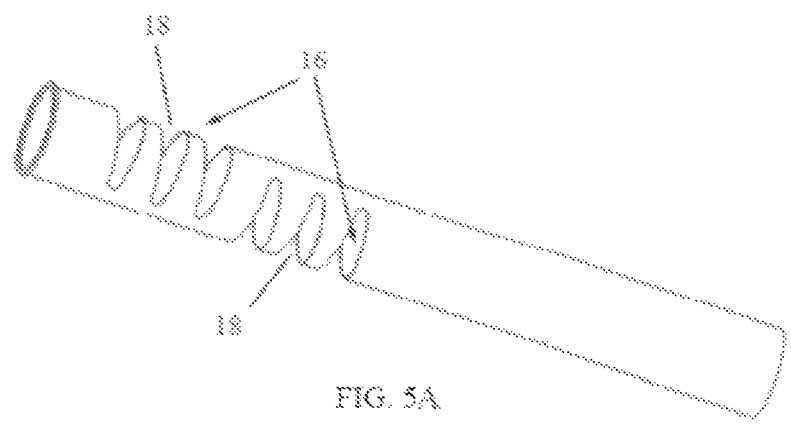
FIGS. 5A and 5B are simplified illustrations of a steering tool, in accordance with another non-limiting embodiment of the present invention, respectively before and after bending, wherein some of the slots face in different directions.
Figure 5B:
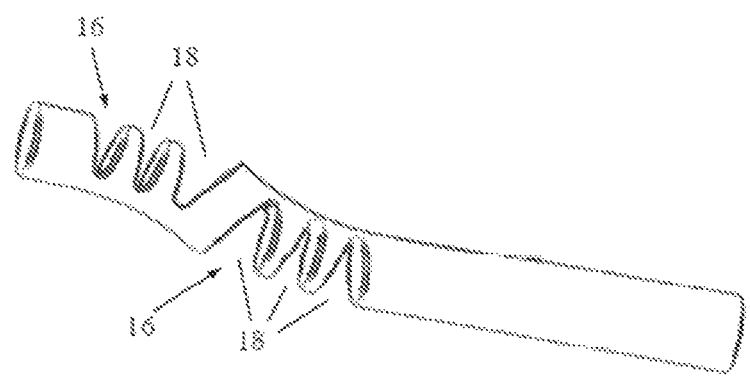

In FIGS. 5A-5B, some of the slots 16 have open ends 18 facing in one direction, while other slots 16 have the open ends 18 facing in another direction, such as 180° apart (although the invention is not limited to this angle). FIG. 5B shows how the tube bends in such a configuration.

Figure 6:
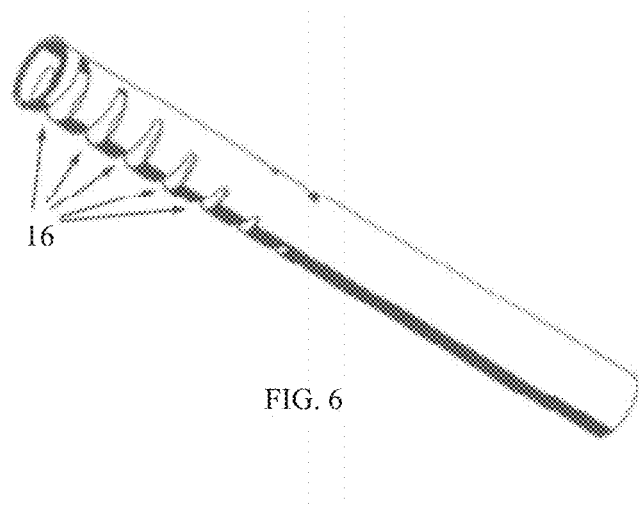
FIG. 6 is a simplified illustration of a steering tool, in accordance with another non-limiting embodiment of the present invention, wherein at least some adjacent slots are circumferentially phase shifted with respect to each other about the circumference of the tube.

In FIG. 6, slots 16 are axially spaced along the distal portion of the tube, but at least some (or all) adjacent slots 16 are circumferentially phase shifted with respect to each other about the circumference of the tube. For example, a first slot may start at some reference point on the circumference, defined as 0°, whereas the next slot may start at 5° and the next one at 10°, etc. The phase shift does not have to be equal (can also be zero for some adjacent slots) and can be ascending, descending or a combination of both.

Slots 16 can be formed by any suitable method, such as but not limited to, machining, cutting, etching, laser cutting and others.

Figure 4:
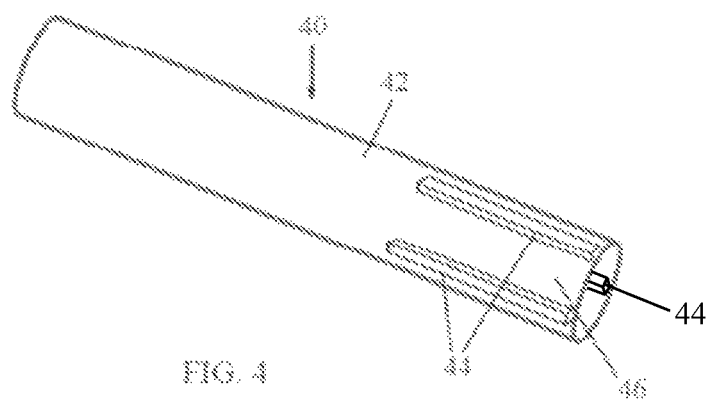
FIG. 4 is a simplified illustration of a steering tool, in accordance with another non-limiting embodiment of the present invention, wherein a slotted tube is replaced by a flexible tube with stiffeners, wherein the stiffeners serve in place of the non-slotted portion and the flexibility serves in place of the slotted portion.

Reference is now made to FIG. 4, which illustrates a steering tool 40, in accordance with a non-limiting embodiment of the present invention. In this embodiment, steering tool 40 includes a flexible tube 42 (e.g., without limitation, made of an extruded material, plastic or metal) with relatively rigid stiffeners 44 (internal or external) at a distal portion 46. Flexible tube 42 replaces the slotted tube of the previous embodiments. The stiffeners 44 serve in place of the non-slotted portion of the previous tubes, and the flexibility of tube 42 serves in place of the slotted portion of the previous tubes.

Figure 7:
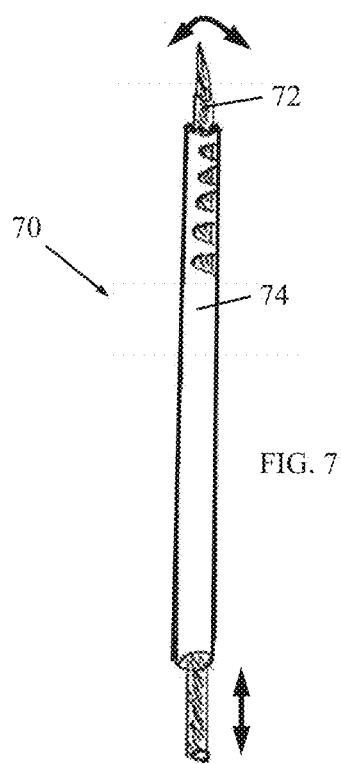
FIG. 7 is a simplified illustration of a steering tool, in accordance with another non-limiting embodiment of the present invention.

Reference is now made to FIG. 7, which illustrates a steering tool 70, in accordance with another non-limiting embodiment of the present invention. In this embodiment, steering tool 70 includes an internal wire 72, that is, an internal non-hollow tube 72, disposed in an external (hollow) tube 74. The distal end of internal tube 72 is flexible (e.g., made with slots or made of a flexible material with relatively rigid stiffeners, as described in the above embodiments) and more flexible than the distal end of external tube 74. The distal end of internal tube 72 is fixedly joined to the distal end of external tube 74. The use of internal non-hollow tube 72 makes possible reaching very small dimensions, such as but not limited to, an overall outer dimension of only 0.3-0.5 mm. Such an embodiment may be used as a steerable guidewire or electrode.

In this embodiment, as well as the other embodiments, the distal edge shape of the internal tube, external tube and/or overall tool may be not only circular, but also shaped as an electrode, needle or other shapes.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A steering tool comprising:
    an internal tube disposed inside an external tube, said internal and external tubes being arranged for longitudinal axial movement relative to one another, wherein a distal end of said internal tube is fixedly joined to a distal end of said external tube, and wherein one of said tubes is flexible with relatively rigid stiffeners at a distal portion thereof, and wherein the longitudinal axial movement causes bending of the distal ends of said tubes, wherein a length of each of said stiffeners extends longitudinally along said one of said tubes parallel to a longitudinal axis of said one of said tubes and said stiffeners are circumferentially spaced from one another.

2. The steering tool according to claim 1, wherein said stiffeners are internal in said one of said tubes.

3. The steering tool according to claim 1, wherein said stiffeners are external on said one of said tubes.

4. The steering tool according to claim 1, wherein said stiffeners extend longitudinally on said one of said tubes.

5. The steering tool according to claim 1, wherein said stiffeners are separate elements from said internal and external tubes.

6. The steering tool according to claim 1, wherein the length of each of said stiffeners extends from a distal end of said one of said tubes to less than half a total length of said one of said tubes.

\* \* \* \* \*